(12) United States Patent
Seaver et al.

(10) Patent No.: US 10,076,643 B2
(45) Date of Patent: Sep. 18, 2018

(54) PRESSURE REGULATING BUOYANT VALVE FOR A SHUNT SYSTEM

(71) Applicant: ARKIS BIOSCIENCES INC., Knoxville, TN (US)

(72) Inventors: Chad Seaver, Knoxville, TN (US); Chris Arnott, Knoxville, TN (US); James Alexander Killeffer, Knoxville, TN (US)

(73) Assignee: Arkis Biosciences Inc., Knoxville, TN (US)

( * ) Notice: Subject to any disclaimer, the term of this patent is extended or adjusted under 35 U.S.C. 154(b) by 217 days.

(21) Appl. No.: 14/964,141

(22) Filed: Dec. 9, 2015

(65) Prior Publication Data

US 2016/0082232 A1 Mar. 24, 2016

Related U.S. Application Data

(63) Continuation-in-part of application No. 13/948,639, filed on Jul. 23, 2013, now Pat. No. 9,381,331.
(Continued)

(51) Int. Cl.
*A61M 27/00* (2006.01)
*A61M 39/22* (2006.01)
*A61M 39/24* (2006.01)

(52) U.S. Cl.
CPC ........ *A61M 27/006* (2013.01); *A61M 39/227* (2013.01); *A61M 39/24* (2013.01);
(Continued)

(58) Field of Classification Search
CPC ....................................... A61M 27/00–27/006
See application file for complete search history.

(56) References Cited

U.S. PATENT DOCUMENTS

| 3,889,687 A | 6/1975 | Harris et al. |
| 4,731,056 A | 3/1988 | Tremulis |

(Continued)

FOREIGN PATENT DOCUMENTS

| EP | 19840400017 | 9/1988 |
| EP | 1587557 | 11/2006 |

(Continued)

OTHER PUBLICATIONS

Integra NeuroSciences; Gravity Compensating Accesory; Integra NeuroSciences Implants S.A., 2002.
(Continued)

*Primary Examiner* — Benjamin Klein
(74) *Attorney, Agent, or Firm* — Meunier Carlin & Curfman LLC

(57) ABSTRACT

A gravitational pressure regulating valve to regulate fluid flow of a patient, including a fluid chamber having an inlet port to receive a bodily fluid and an outlet port to discharge received bodily fluid, the fluid chamber including a first chamber configured to capture a non-buoyant member therein and to guide the non-buoyant member along a longitudinal axis of the first chamber to facilitate bi-directional reciprocating movement of the non-buoyant member to and from the inlet port, and a second chamber configured to capture one or more buoyant members therein such that when the second chamber is filled with bodily fluid, at least one of the buoyant members applies a resolved buoyant pressure from a buoyant force of the one or more buoyant members in opposition to an inlet pressure of fluid at the inlet port.

16 Claims, 10 Drawing Sheets

Related U.S. Application Data

(60) Provisional application No. 61/674,729, filed on Jul. 23, 2012.

(52) U.S. Cl.
CPC . *A61M 2039/242* (2013.01); *A61M 2039/248* (2013.01); *A61M 2210/0693* (2013.01); *A61M 2230/62* (2013.01)

(56) References Cited

U.S. PATENT DOCUMENTS

| | | |
|---|---|---|
| 5,368,556 A | 11/1994 | Lecuyer |
| 5,437,627 A | 8/1995 | Lecuyer |
| 5,527,295 A | 6/1996 | Wing |
| 5,634,894 A | 6/1997 | Magram |
| 6,383,160 B1 | 5/2002 | Madsen |
| 6,953,444 B2 | 10/2005 | Rosenburg |
| 7,282,040 B2 | 10/2007 | Hokanson |
| 8,088,092 B2 | 1/2012 | McCusker et al. |
| 2002/0026139 A1 | 2/2002 | Bertrand |
| 2005/0038371 A1 | 2/2005 | Reich et al. |
| 2006/0089589 A1* | 4/2006 | Portnoy ............ A61M 27/002 604/9 |

FOREIGN PATENT DOCUMENTS

| | | |
|---|---|---|
| EP | 1613388 | 2/2008 |
| FR | 2793417 | 11/2000 |

OTHER PUBLICATIONS

PCT: International Search Report (PCT Article 18 and Rules 43 and 44); dated Nov. 22, 2013; International Searching Authority.

Office Action issued in co-pending Japanese Application No. 2015-524387, dated May 29, 2017.

Office Action dated Apr. 5, 2018, issued in corresponding Mexico Application No. MX/a/2015/001086, 8 pages.

Letter from MX associate summarizing Apr. 5, 2018 Office Action in corresponding MX Application No. Mx/a/2015/001086 (cited above).

* cited by examiner

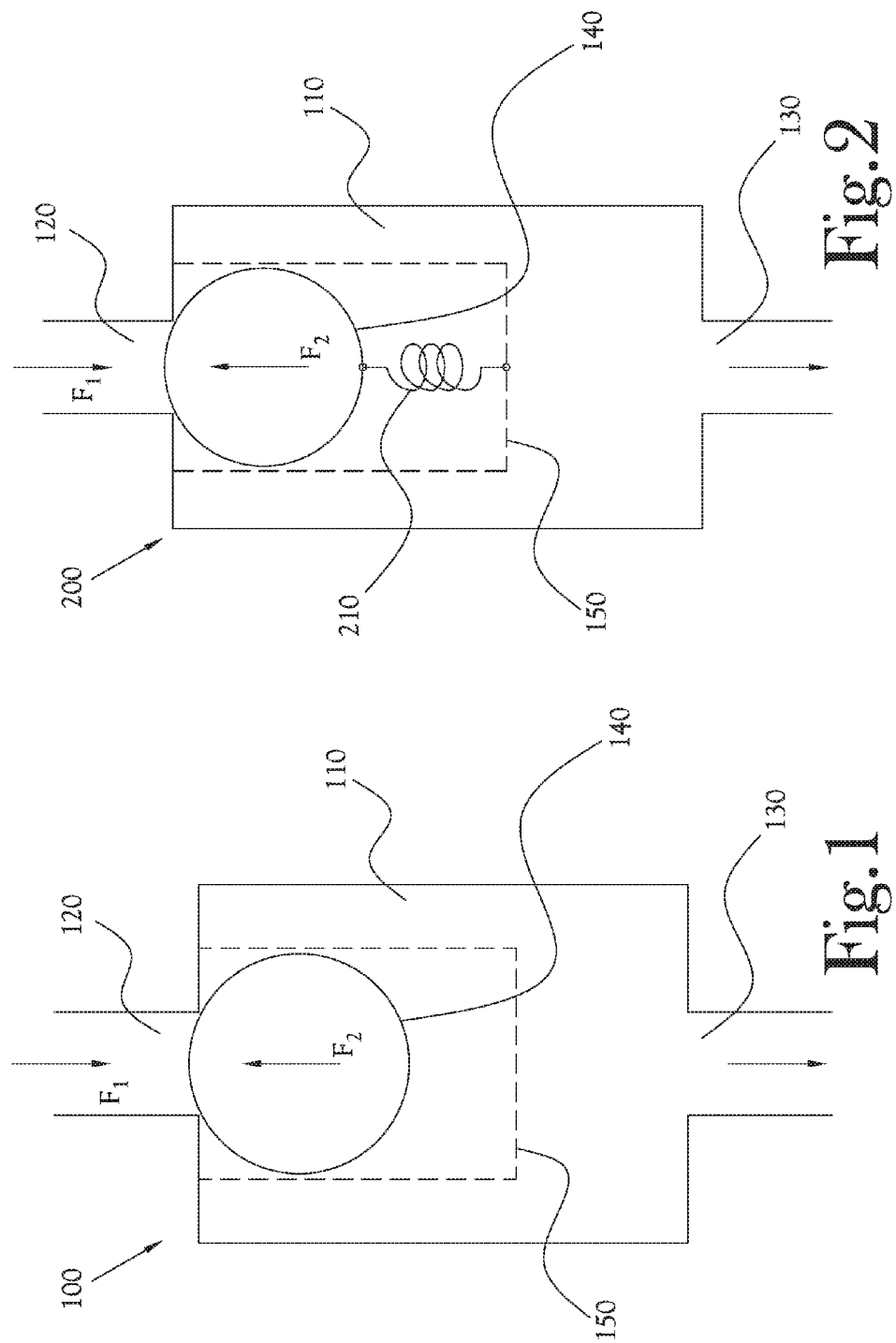

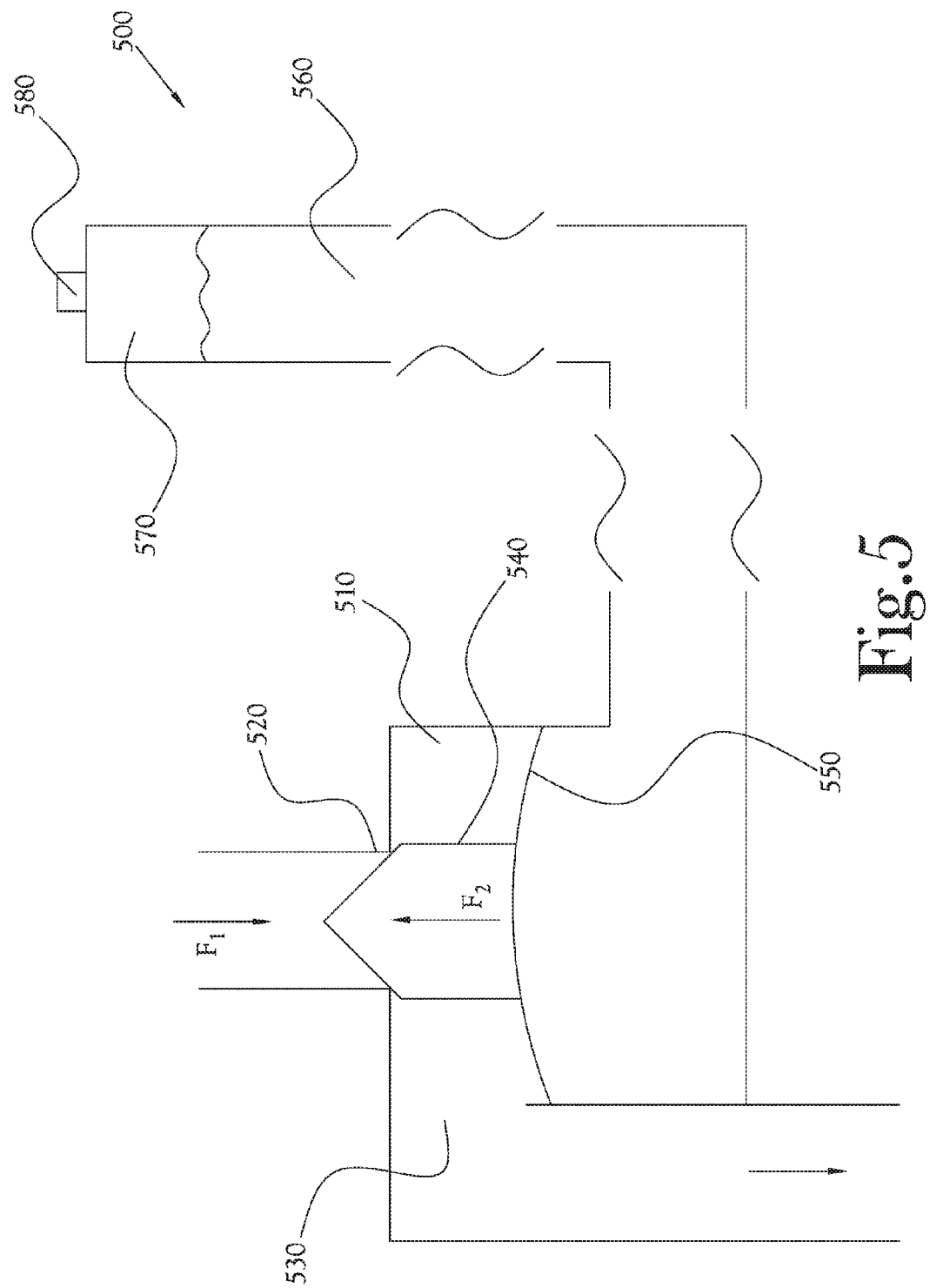

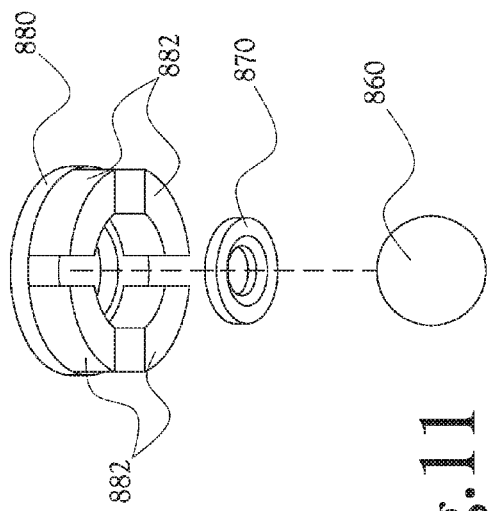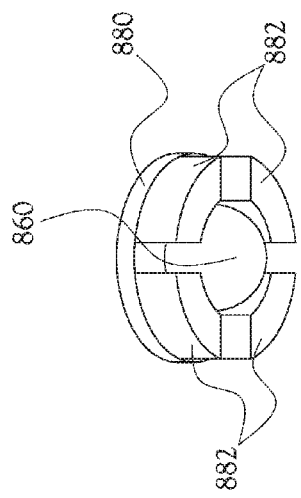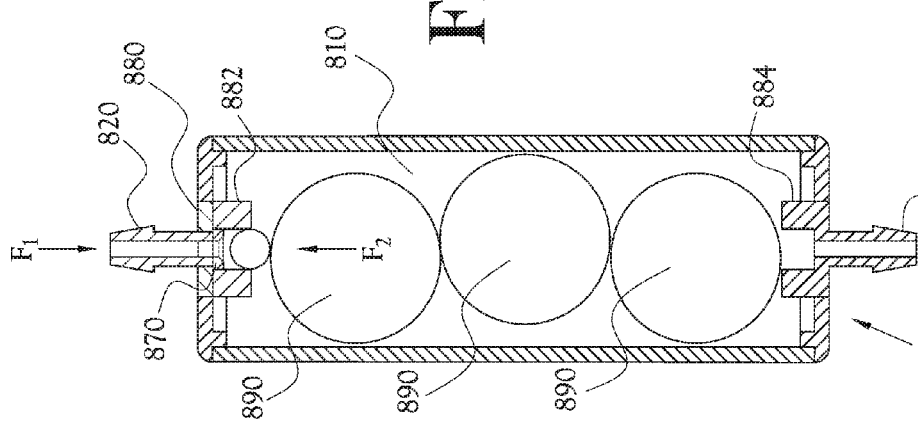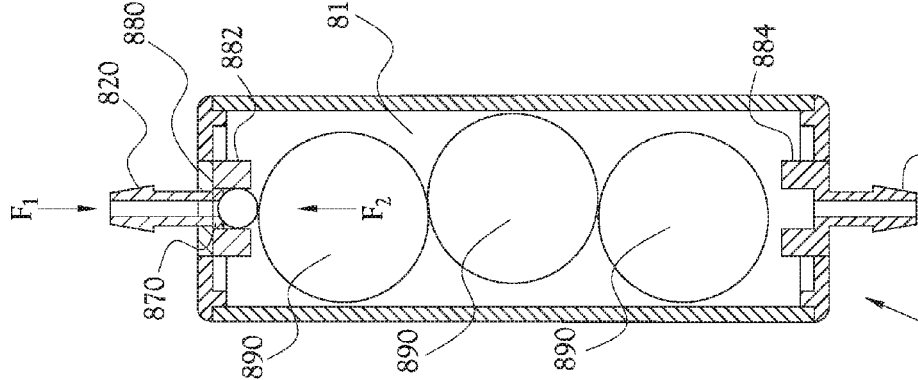

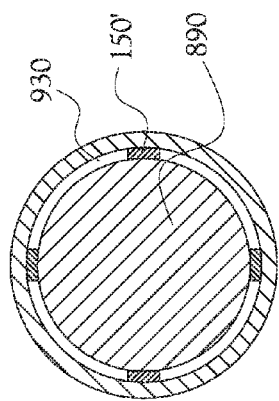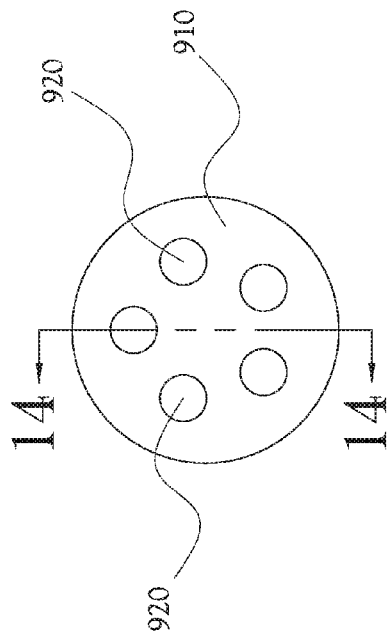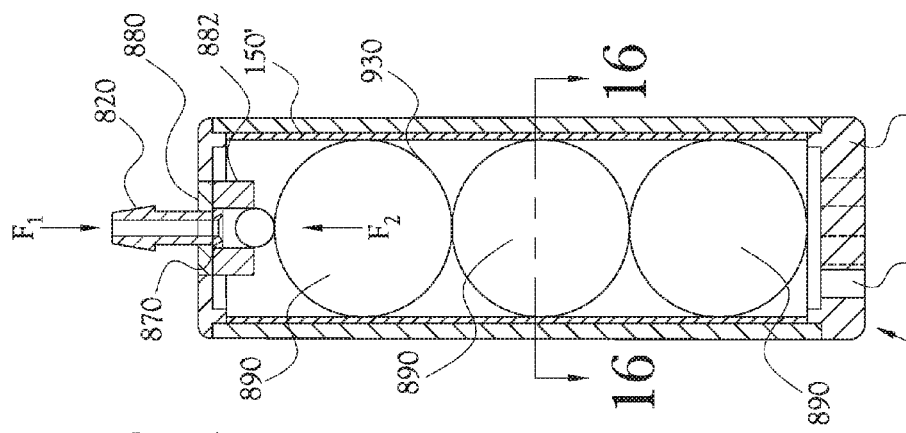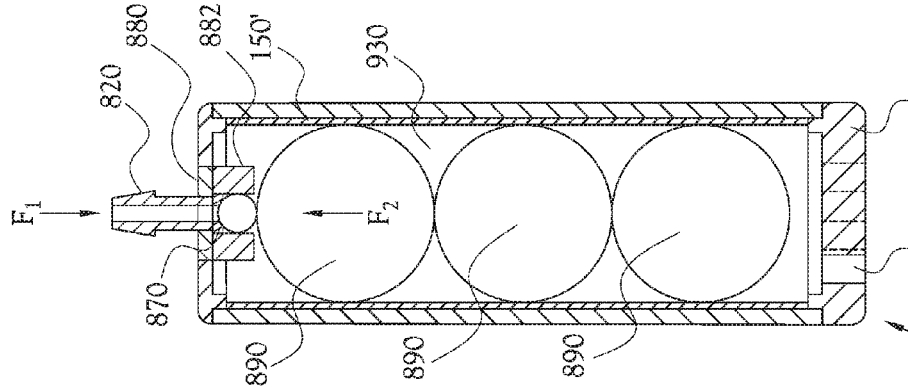

PRESSURE REGULATING BUOYANT VALVE FOR A SHUNT SYSTEM

CROSS-REFERENCE TO RELATED APPLICATIONS

This application is a Continuation-In-Part of U.S. application Ser. No. 13/948,639, filed on Jul. 23, 2013, which claims the benefit of U.S. Provisional Application No. 61/674,729, filed on Jul. 23, 2012, the disclosures of which are incorporated herein by reference in their entirety.

FIELD OF INVENTION

The present general inventive concept relates generally to a pressure regulating valve in a shunt system, and, more particularly, to a pressure regulating valve to compensate for the force of gravity on bodily fluid in a shunt system that occurs when a patient is upright.

BACKGROUND

The human cranial vault contains the brain, blood vessels, and cerebrospinal fluid (CSF). The sutures of the cranium fuse by a year of age and the skull becomes a rigid structure. The architecture and physiology of the intracranial space allow for some compensation for additional intracranial volume such as hemorrhage, tumor, or excess CSF. When this compensatory capacity is exhausted, the contents act essentially as ideal fluids in a rigid container, making them subject to rapid rises in pressure when a relatively small volume of fluid is added. With sufficient rise in intracranial pressure (ICP), brain tissue is compressed and its blood supply is compromised resulting in brain damage and, if unchecked, death.

In the normal brain, CSF is secreted by tissue known as choroid plexus within cavities in the brain called ventricles. The CSF flows from the uppermost lateral ventricles through conduits into the more central third and then fourth ventricles, then flowing out of the brain to surround the spinal cord and brain. Ultimately, the CSF is absorbed on the outer surface of the brain by cells comprising the arachnoid villi. This is a continuous circulation, amounting to approximately 400 cc/day. Any interruption in CSF circulation can result in excess CSF within the intracranial space, a condition known as hydrocephalus. In mild cases, CSF fills the ventricles excessively and stretches the cells of the brain resulting in neurological dysfunction. In severe cases, the rise in ICP may be sufficient to result in brain damage or death.

The most common contemporary treatment of hydrocephalus is to divert the flow of CSF. CSF is diverted to a space in the body that has a large capacity to absorb it such as the peritoneum, pleura, or bloodstream. A shunt for CSF diversion typically consists of a synthetic tube placed through a hole drilled in the skull and passed through the brain and terminates in the desired drainage location. Lumboperitoneal shunting is also possible, which avoids the need to drill into the skull by instead draining CSF from the lumbar region of spinal column, but is at greater risk of siphoning. The shunt may be fitted with a valve designed to control pressure and flow as well as a device designed to retard over-drainage due to siphoning with upright posture.

Currently available shunt technology has several shortcomings. Valve technology is often inadequate to provide the optimal level of drainage. Under-drainage results in elevated ICP and over-drainage can result in headaches or hemorrhage due to collapse of the brain and tearing of surface blood vessels. Differential pressure based shunts, even with "anti-siphon countermeasures," often do not adapt well to changes in posture, to fluctuating CSF production and ICP, or to changes in intracranial CSF dynamics over time. Patients with shunts and persistent headaches frequently present a challenge because it is unclear whether there is subtle over- or under-drainage. The simple externally adjustable valves available currently force the clinician to guess at the appropriate pressure setting and accept that the system cannot adapt to fluctuations in demand.

CSF siphoning occurs when patient position results in additional pressure in the shunt due to gravitational forces acting upon the fluid column within the shunt and its tubing. This excess pressure is exerted across the shunt's differential valve, causing it to activate and undesirably allow CSF fluid to flow. This unwanted parasitic flow can reduce patient quality of life and can lead to numerous serious life threatening conditions by excess removal of CSF from the patient's brain. A significant source of this unwanted siphoning is the error pressure, as viewed from the valve, generated by the force, or resulting pressure, produced by the weight of the CSF fluid contained within the shunt tubing between the proximal catheter, the shunt tubing, and the distal catheter exit. Such error pressure is at a maximum when the patient is in the upright position, whereby the shunt's tubing is in general alignment with the gravitational field, and conversely is at a minimum when the patient is in a supine position and the tube is perpendicular to the gravitational field. The taller the patient, the worse the siphoning effect generally is, and such siphoning occurs in generally any position other than lying down (i.e., the supine position).

In the case of lumboperitoneal shunting, the CSF contained within the spinal column is the source of the error pressure generation. The pressure generated by the weight of the CSF in the spinal column can easily exceed the set point of differential valves in the shunt and lead to siphoning. A patient's motion and position affects how much error pressure is generated; minimum siphoning occurs when the patient and the shunt's flow path are supine, and maximum siphoning occurs when upright. This parasitic siphoning is a reason why the less costly and less complex surgical procedure of lumboperitoneal shunt treatment is not a more prevalent treatment option for hydrocephalus. Thus, there exists a desire for an anti-siphon device that prevents over drainage of CSF fluid regardless of patient position or activity.

BRIEF SUMMARY

The present general inventive concept provides a gravitational pressure regulating valve to regulate fluid flow of a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by a gravitational pressure regulating valve to regulate fluid flow of a patient, including a fluid chamber having an inlet port to receive a bodily fluid and an outlet port to discharge the received bodily fluid, and a buoyant member provided in the fluid chamber and configured to oppose a first force of the fluid flow at the inlet port with a second force that varies according to changes in gravitational field alignment in the fluid chamber due to the orientation of the valve.

The buoyant member may be configured to close the inlet port in response to the second force exceeding the first force.

The buoyant member may be substantially spherical.

The gravitational pressure regulating valve may further include a permeable guide member provided in the fluid chamber and configured to allow bidirectional movement of the buoyant member within the guide member.

The gravitational pressure regulating valve may further include a biasing member coupled to the buoyant member and the guide member to augment the second force.

The gravitational pressure regulating valve may further include one or more additional buoyant members to augment the second force.

The gravitational pressure regulating valve may further include a guide member coupled to the fluid chamber and the buoyant member to guide the buoyant member to and from the inlet port in a substantially reciprocating path.

The second force may have a maximum value in response to the inlet port being directly above the one or more buoyant members.

The buoyant member may remain substantially seated in and centrally aligned with the inlet port regardless of the orientation of the valve.

The foregoing and/or other aspects and advantages of the present general inventive concept may also be achieved by a gravitational pressure regulating valve to regulate fluid flow of a patient, including a fluid chamber having an inlet port to receive a bodily fluid and an outlet port to discharge the received bodily fluid, and a plurality of weighted members provided in the fluid chamber and configured to oppose a first force of the fluid flow at the inlet port with a second force that varies according to changes in gravitational alignment of the weighted members due to the orientation of the valve, wherein at least a portion of an inner surface of the fluid chamber is configured to be substantially conical around the inlet port such that a first one of the weighted members closest to the inlet port is offset from any remaining weighted members in the direction of the inlet port.

The first one of the weighted members may be configured to close the inlet port in response to the second force exceeding the first force.

The weighted members may be substantially spherical.

The second force may have a maximum value in response to the inlet port being directly below the first one of the weighted members.

The fluid chamber may be configured to limit movement of the weighted members such that the first one of the weighted members will remain closest to the inlet port regardless of the orientation of the valve.

The fluid chamber may be configured to limit movement of the weighted members such that the first one of the weighted members will always be in contact with at least one remaining weighted member.

The second force may be a combination of vector forces from each of the weighted members in response to the inlet port being directly below the first one of the weighted members.

The weighted members may each be configured to have a greater density than the bodily fluid moving in and out of the fluid chamber.

The foregoing and/or other aspects and advantages of the present general inventive concept may also be achieved by a gravitational pressure regulating valve to regulate fluid flow of a patient, including a fluid chamber having an inlet port to receive a bodily fluid and an outlet port to discharge the received bodily fluid, a variable resistance flow valve provided in the fluid chamber and configured to oppose a first force of the fluid flow at the inlet port with a second force applied to the variable resistance flow valve, an opposing force member configured to apply the second force to the variable resistance flow valve, and a reference unit sensitive to gravitational alignment changes to cause the opposing force member to vary the second force according to the gravitational alignment changes.

The opposing force member may be a diaphragm coupled to the variable resistance flow valve.

The reference unit may include a reference fluid column in direct communication with the diaphragm, the diaphragm may separate the bodily fluid and fluid from the reference fluid column, and the reference fluid column may be configured such that changes in the gravitational alignment of the reference fluid column correspond to changes in the gravitational pressure at the inlet port.

The gravitational pressure regulating valve may further include a predetermined amount of gas forming an interface with the reference fluid column to allow compression in the diaphragm resulting from an opening of the variable resistance flow valve.

The gravitational pressure regulating valve may further include a housing to house the reference fluid column and gas, and an air bleeder port to remove air from the housing when the housing is being filled with liquid.

The reference unit may include a gravitational alignment sensor, and may be in electrical communication with the opposing force member to cause the opposing force member to vary the second force according to the gravitational alignment changes.

The foregoing and/or other aspects and advantages of the present general inventive concept may also be achieved by a gravitational pressure regulating valve to regulate fluid flow of a patient, including a fluid chamber having an inlet port to receive a bodily fluid and an outlet port to discharge received bodily fluid, the fluid chamber including a first chamber configured to capture a non-buoyant member therein and to guide the non-buoyant member along a longitudinal axis of the first chamber to facilitate bi-directional reciprocating movement of the non-buoyant member to and from the inlet port, and a second chamber configured to capture one or more buoyant members therein such that when the second chamber is filled with bodily fluid, at least one of the buoyant members applies a resolved buoyant pressure from a buoyant force of the one or more buoyant members in opposition to an inlet pressure of fluid at the inlet port.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIG. 1 illustrates a gravitational pressure regulating valve according to an example embodiment of the present general inventive concept;

FIG. 2 illustrates the valve of FIG. 1 with an auxiliary bias member according to an example embodiment of the present general inventive concept;

FIGS. 5-6 illustrate a gravitational pressure regulating valve according to yet another example embodiment of the present general inventive concept;

FIGS. 9-10 illustrate a cross section of the gravitational pressure regulating valve of FIG. 8 in closed and open states, respectively, at the inlet port;

FIGS. 11-12 respectively illustrate an exploded view and an assembled view of the retaining chamber, mating cone seat, and precision net non-buoyant ball illustrated in FIGS. 9-10 according to an example embodiment of the present general inventive concept;

FIGS. 14-15 illustrate a cross section of the gravitational pressure regulating valve 900 of FIG. 13 in closed and open states, respectively, at the inlet port;

FIG. 16 illustrates a cross section of the fluid chamber, fluid chamber guide members, and buoyant members of FIGS. 13-15 according to an example embodiment of the present general inventive concept; and FIG. 17 illustrates a bottom view of the outlet port 910 of FIGS. 13-15 according to an example embodiment of the present general inventive concept.

DETAILED DESCRIPTION

Figure 3:
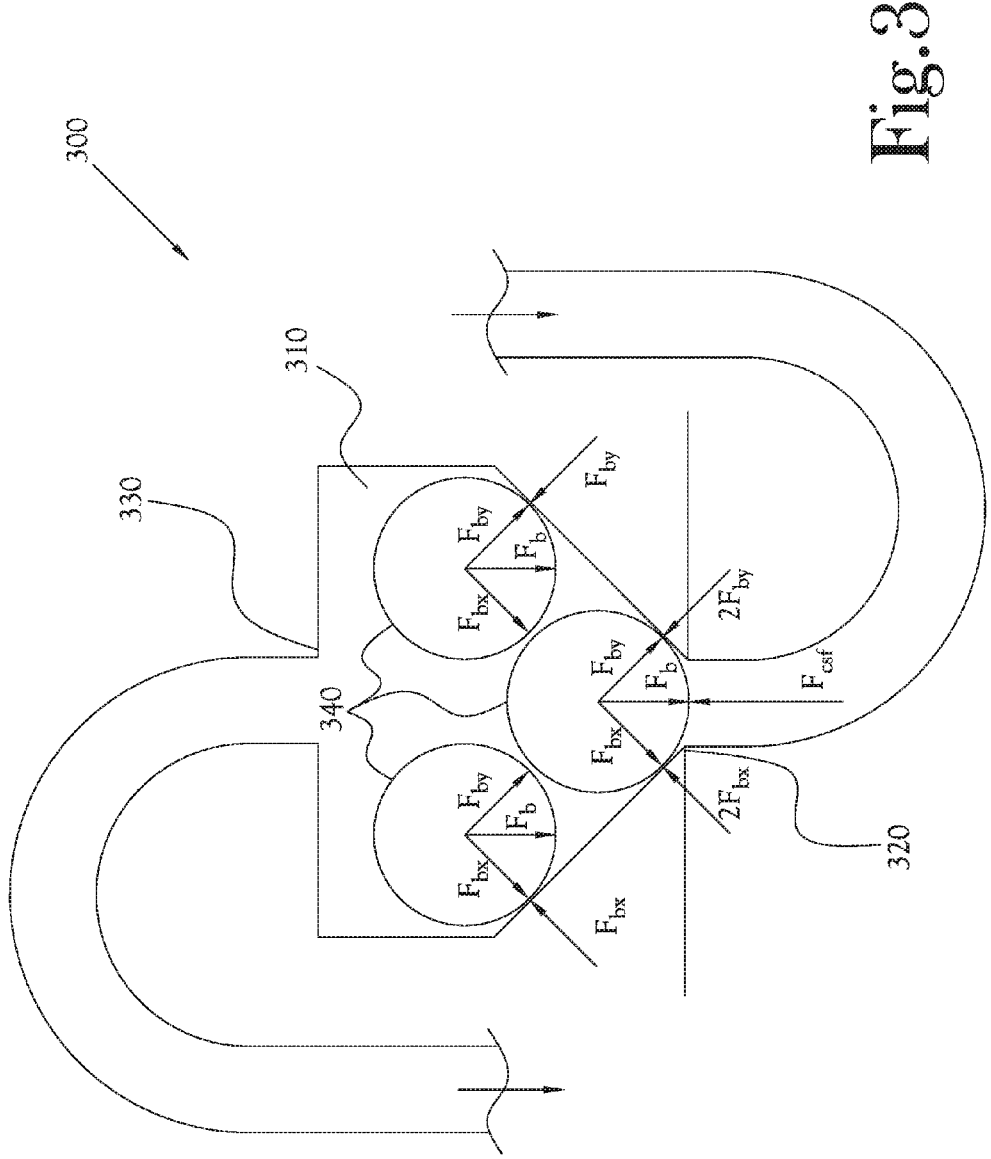
FIG. 3 illustrates a gravitational pressure regulating valve according to another example embodiment of the present general inventive concept.

Reference will now be made to various example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Various example embodiments of the present general inventive concept, as described herein, provide a gravitational pressure regulating valve to regulate fluid flow in a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment. Various example embodiments of the present general inventive concept may employ one or more buoyant and/or weighted elements acting directly on an inlet port to counter a fluid pressure increase caused by increased gravitational pull that occurs when a patient moves from a supine to an upright position. In various example embodiments, the terms "weighted" and "non-buoyant" may be used interchangeably when referring to the elements acting to counter the fluid pressure at the inlet port that are not net buoyant (i.e., do not float) in the bodily fluid entering the gravitational pressure regulating valve. Similarly, the term "buoyant" may be used interchangeably with the term "net buoyant" when referring to one or more elements that do float in the bodily fluid entering the gravitational pressure regulating valve. Other various example embodiments of the present general inventive concept may employ a valve that is controlled by other gravity sensitive elements.

Although various example embodiments of the present general inventive concept provide a gravitational pressure regulating valve to regulate fluid flow in a patient, the descriptions herein may generally describe a CSF flow regulating device to prevent siphoning in a hydrocephalus shunt system. However, it is understood that various example embodiments of the present general inventive concept may be used to regulate other types of fluid flow in other types of procedures and/or systems. Also, while fluid flow "in" a patient may be discussed in the descriptions of various example embodiments of the present general inventive concept, it is understood that embodiments of the present general inventive concept may be utilized inside and/or outside of the patient, and therefore the fluid flow being regulated could be occurring inside and/or outside of the patient.

With reference to the following descriptions of the drawings, there is generally illustrated and described an antisiphon device. Various example embodiments of the present general inventive concept can be utilized to realize an antisiphon device that prevents unwanted CSF siphoning in a hydrocephalus shunt treatment. The present general inventive concept alleviates various limitations associated with the conventional hydrocephalus shunt CSF siphoning problems with a novel antisiphon device that aids in preventing CSF siphoning regardless of patient position. The gravitational pressure regulating valve according to various example embodiments of the present general inventive concept may be incorporated into existing hydrocephalus shunt systems already in place in a patient. For example, the gravitational pressure regulating valve may simply be applied at the distal end of an existing shunt system to compensate for the increased force that gravity provides to CSF flow when a patient is upright. In other words, a device according to an embodiment of the present general inventive concept may be retrofitted to an existing system with a relatively simple surgery.

FIG. 1 illustrates a gravitational pressure regulating valve according to an example embodiment of the present general inventive concept. The gravitational pressure regulating valve 100 of FIG. 1 includes a fluid chamber 110 having an inlet port 120 and an outlet port 130, and a buoyant member 140 provided in the fluid chamber 110. Fluid flows into the inlet port 120 at a first force F1, and the buoyant member 140 opposes the fluid flow with a second force F2. Either, or both, of the resolved resultant forces F1 and/or F2 may be alternatively equated to a fluid pressure by conversion into their equivalent components of force per unit area. For example, various example embodiments of the present general inventive concept described herein may refer to a buoyant force of one or more buoyant members in opposition to an inlet force of fluid pressure at the inlet port, such as the fluid pressure resulting from static, dynamic, and/or head pressure, and such forces may be equated to resolved buoyant pressure and inlet pressure, respectively. Force F1 can include both dynamic and/or static fluid pressure at the inlet port, as well as head pressure (i.e., gravitational pressure) contributing to the inlet force F1. Both of the forces F1 and F2 may vary according to changes in the pressure acting on the system caused by changes in gravitational field alignment. In other words, as changes occur in the gravitational field alignment, accumulated weight of the fluid may increase the first force F1, and a component of the buoyant force vector of the buoyant member 140 in the fluid chamber may increase the second force F2. For example, the force F1 of the fluid, or its flow, includes the normal intracranial drainage force which moves the CSF from the cranium of the patient, but the force F1 is increased when the patient is upright, due to the extra force gravity is placing on the fluid. Therefore, to counter the effects that gravity has on F1, the gravitational alignment of the buoyant member 140 with respect to the inlet port 120 increases the seating force of the buoyant member 140, and therefore the opposing force F2 is increased. In other words, the forces F1 and F2 approach their maximum values when the patient and valve are completely vertical. When the patient is in a horizontal position, the gravitational effect of F1 and F2 approach their minimum values. The changes in these forces caused by gravitational alignment and the weight of the fluid may be generally referred to as changes in gravitational pressure in the descriptions of various example embodiments of the present general inventive concept. Various example embodiments may be generally referred to herein as a buoyant gravitational valve when the valve contains one or more buoyant members.

When the opposing second force F2 is equal to or exceeds the first force F1, the buoyant force on the buoyant member 140 causes the buoyant member 140 to move to close or increase a closing pressure upon the inlet port 120, as illustrated in FIG. 1. By contrast, when the first force F1 exceeds the opposing second force F2, the buoyant member 140 is moved to open the inlet port 120, at which point the bodily fluid will flow until the first force F1 is again matched or exceeded by the second force F2. As illustrated in FIG. 1, the buoyant member 140 may be substantially spherical. Although not illustrated in FIG. 1, the inlet port 120 may be configured to readily accept the curved surface of the buoyant member 140 in order to form an improved seal to prevent leakage of the bodily fluid through the inlet port 120. In various example embodiments of the present general inventive concept, the buoyant member 140 may remain substantially seated in and centrally aligned with the inlet port regardless of valve orientation.

The gravitational pressure regulating valve 100 may also include a guide member in the fluid chamber 110 to facilitate movement of the buoyant member 140 in a substantially bidirectional manner. In other words, the guide member may cause the buoyant member 140 to move only directly to and away from the inlet port 120, to prevent the buoyant member 140 from moving to a position that inhibits the closing of the inlet port 120. In the example embodiment illustrated in FIG. 1, a permeable guide member 150 is provided in the form of a cage that guides the buoyant member 120 to and away from the inlet port 120. In this example embodiment, the guide member 150 can be constructed of a permeable material, and may be generally referred to as a permeable member in some of the descriptions herein, but is not limited to this or any other particular type of material. The permeable guide member 150 may be cylindrical, and configured to have a diameter only slightly larger than that of the buoyant member 140, to further limit any movement not associated with the reciprocating opening and closing of the valve. Such a configuration in which a fit of the guiding member is only slightly larger than the outer dimension of the guided member is commonly referred to by one skilled in the art as a slip fit. The diameter of the permeable guide member 150 may be sufficiently smaller than that of the fluid chamber 110 such that a desired amount of fluid may surround the buoyant member 140 inside the fluid chamber 110. The opposing force, F2, created by the buoyancy member 140, results in an opposition proportional to the gravitational angle of the buoyancy member 140, relative to the permeable guide member 150 and inlet port 120, whereby the force vector F2 becomes a component of the overall buoyancy force which is in alignment with the gravitational field. Therefore, the opposing force, F2, gradually reduces as the patient reclines to a minimum in the horizontal position, relative to the gravitational field and then gradually to a maximum when in a standing position.

In a situation in which the patient and valve are horizontal, the gravitational component of the second force F2 approaches zero. Therefore, to adjust the opposing second force F2 such that a desired second force F2 exists in the supine position, additional elements may be added to augment the second force F2. FIG. 2 illustrates the valve of FIG. 1 with an auxiliary bias member according to an example embodiment of the present general inventive concept. The auxiliary bias member is in the form of a spring 210 which couples the buoyant member 140 to the permeable guide member 150 and biases the buoyant member 140 in the direction of the inlet port 120. Thus, when the patient and valve are in the horizontal position, the force provided by the spring 210 may be the only component of the second force F2. In situations in which the patient is more upright than the horizontal position, the buoyant force resulting from the increased gravitational pressure is combined with the force of the spring to result in the total second force F2. With the additional opposing force provided by the biasing member, the bodily fluid does not freely flow into the fluid chamber 110 in the event that no buoyant force is present on the buoyant member 140. As a result, the bodily fluid may flow at the desired rate by only overcoming the biasing force of the spring 210 when the patient is supine, but additional gravitational force on the bodily fluid is countered by a proportional counterforce due to the buoyant force on the buoyant member 140 when the patient is more upright.

While only one buoyant member 140 is illustrated in FIGS. 1-2, it is understood that two or more buoyant members may be provided inside the fluid chamber 150 to provide additional buoyant force to the opposing second force F2. In an embodiment in which the permeable guide member is provided, the two or more buoyant members may be provided in line inside the guide member.

Figure 4A:
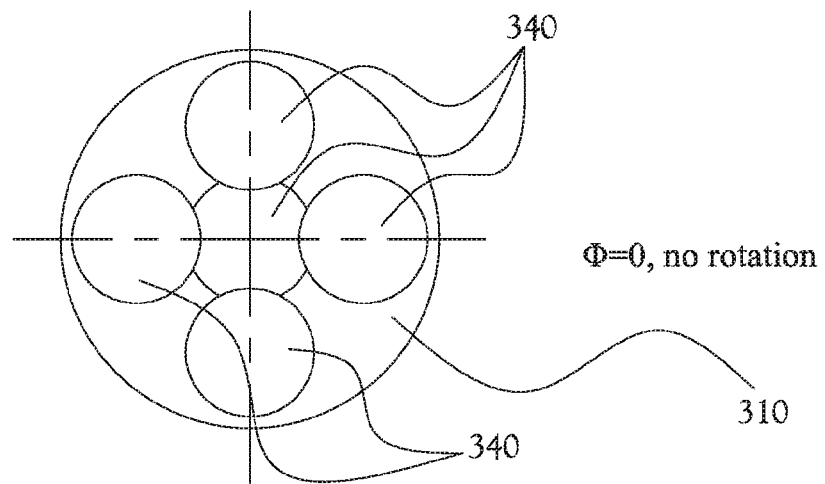
FIGS. 4A-C illustrate a top view of the opposing force members illustrated in FIG. 3 at varying degrees of rotation of the gravitational pressure regulating valve.
Figure 4B:
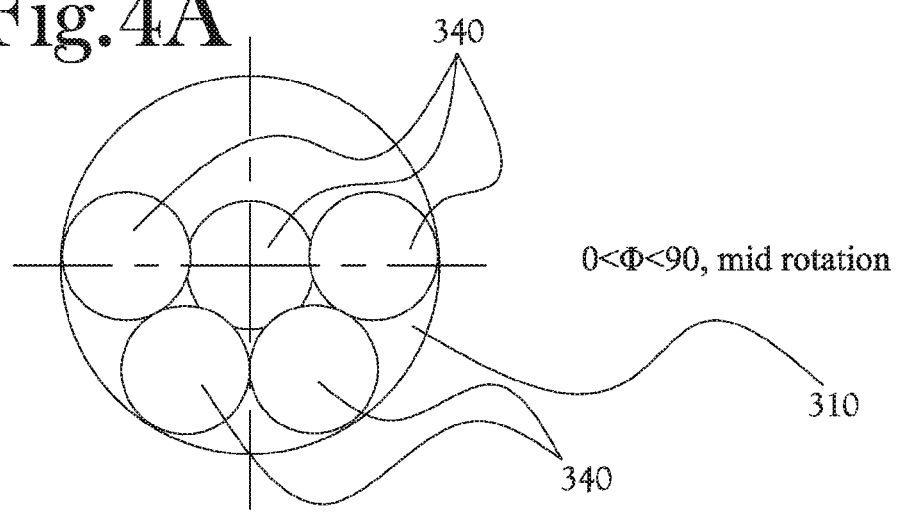
Figure 4C:
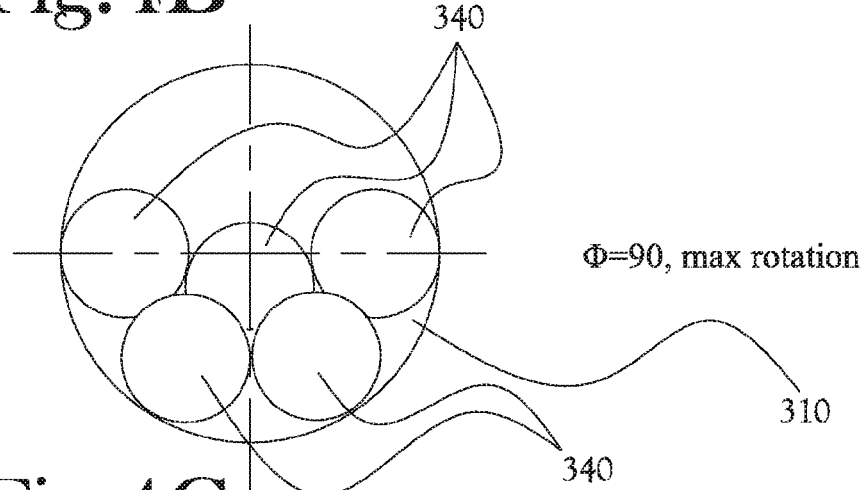

FIG. 3 illustrates a gravitational pressure regulating valve according to yet another example embodiment of the present general inventive concept, and FIGS. 4A-C illustrate a top view of the opposing force members illustrated in FIG. 3 at varying degrees of rotation of the gravitational pressure regulating valve. The example embodiments of FIGS. 1-2 are configured such that the bodily fluid enters an inlet port at or near the top of the valve when oriented in a vertical position, and therefore employ buoyant members to provide a counter force to the fluid flow. By contrast, the example embodiment of FIGS. 3-4C is configured such that the bodily fluid enters an inlet port at or near the bottom of the valve when oriented in a vertical position, and therefore employs weighted members having a greater density than the bodily fluid, so that the weight of the weighted members provides the counter force. Thus, while the embodiments illustrated in FIGS. 1-4C are all illustrated in the most vertically oriented positions, the bodily fluid flows down through the inlet port into the fluid chamber in FIGS. 1-2, while the bodily fluid flows up through the inlet port into the fluid chamber in FIGS. 3-4C. However, it is understood that, as indicated in the drawings, the origin of the bodily fluid is "above" the valves in all of the drawings, and is simply routed by the tubing to enter the valves from the underside in the example embodiment illustrated in FIGS. 3-4C.

The example embodiment of the gravitational pressure regulating valve 300 illustrated in FIG. 3 includes a fluid chamber 310 with an inlet port 320 to receive a bodily fluid and an outlet port 330 to discharge the received bodily fluid, and a plurality of weighted members 340 in the fluid chamber to oppose a first force F1 of the fluid flow at the inlet port 320 with an opposing second force F2 that varies according to changes in the gravitational pressure on the weighted members 340 due to the orientation of the valve. In FIG. 3, the first force F1 is represented as $F_{csf}$, the force of CAF siphoning, and the second force F2 is represented as $F_b$, which is generated by the weighed members 340. As illustrated in FIG. 3, at least a portion of an inner surface of the fluid chamber 310 is provided in a substantially conical shape around the inlet port 320 such that a first one of the weighted members 340 is guided by gravity to rest in and close the inlet port 320 when the second force F2 is greater than the first force F1. Also, the conical shape of the inner surface of the fluid chamber 310 causes the remaining weighted members 340 to be offset in a horizontal and vertical direction from the first weighted member 340. As illustrated in this embodiment, the weighted members may be substantially spherical.

As illustrated in FIG. 3, the gravitational forces of the weighted members in the direction of the second force F2 can be viewed as component force vectors in the x and y directions indicated in the drawing. Due to the first weighted member 340 being offset in the vertical and horizontal directions from the remainder of the weighted members 340, portions of the total gravitational forces from those weighted members 340 are added to the opposing force provided by the weight of the first weighted member 340. Thus, not only is the total opposing second force F2 increased by such an arrangement, but more stability is provided to the closing force when the valve is tilted away from the vertical orientation, until the valve is horizontal, at which point the gravitational force of the weighted members 340 is at a minimum value. The center of mass generated by the plurality of the weighted members 340 counters the force due to siphoning when the patient is upright from the horizontal position. That center of mass shifts with incline angle until the minimum opposing force is produced at the horizontal position, at which the desired fluid set point should control the opening of the inlet port 320. Various values of either the number or the size of the weighted members can be selected to compensate for patient height.

FIG. 4A is a top view of a partial cross section of the valve of FIG. 3. In this drawing, the valve is at a vertical orientation, and therefore the first weighted member 340 is closing the inlet port 320, and the remaining weighted members 340 are providing substantially equal weights to the first weighted member 340. At this vertical orientation, indicated as having "no rotation" in the drawing, the combined center of mass of the weighted members 340 opposes the first force F1 that is the effect of siphoning. Due to the configuration of the weighted members 340 and the conical inner surface of the fluid chamber 310, the opposing force is proportional to the rotation of the valve, as is the force F1 due to the bodily fluid siphoning. As illustrated in FIGS. 4B-C, the shifting center of mass of the weighted members 340 opposes, or counters, the first force F1 due to siphoning as the rotation angle increases. In FIG. 4C, at the maximum rotation, or horizontal position, the opposing second force F2 has reached the minimum magnitude.

It is noted that while five weighted members 340 have been illustrated in the example embodiment described above, various other example embodiments of the present general inventive concept may utilize more or less of the weighted members. Also, various example embodiments may provide a fluid chamber 310 that is formed to limit the movement of the weighted members such that the first one of the weighted members will always be in contact with at least one remaining weighted member.

Figure 6:
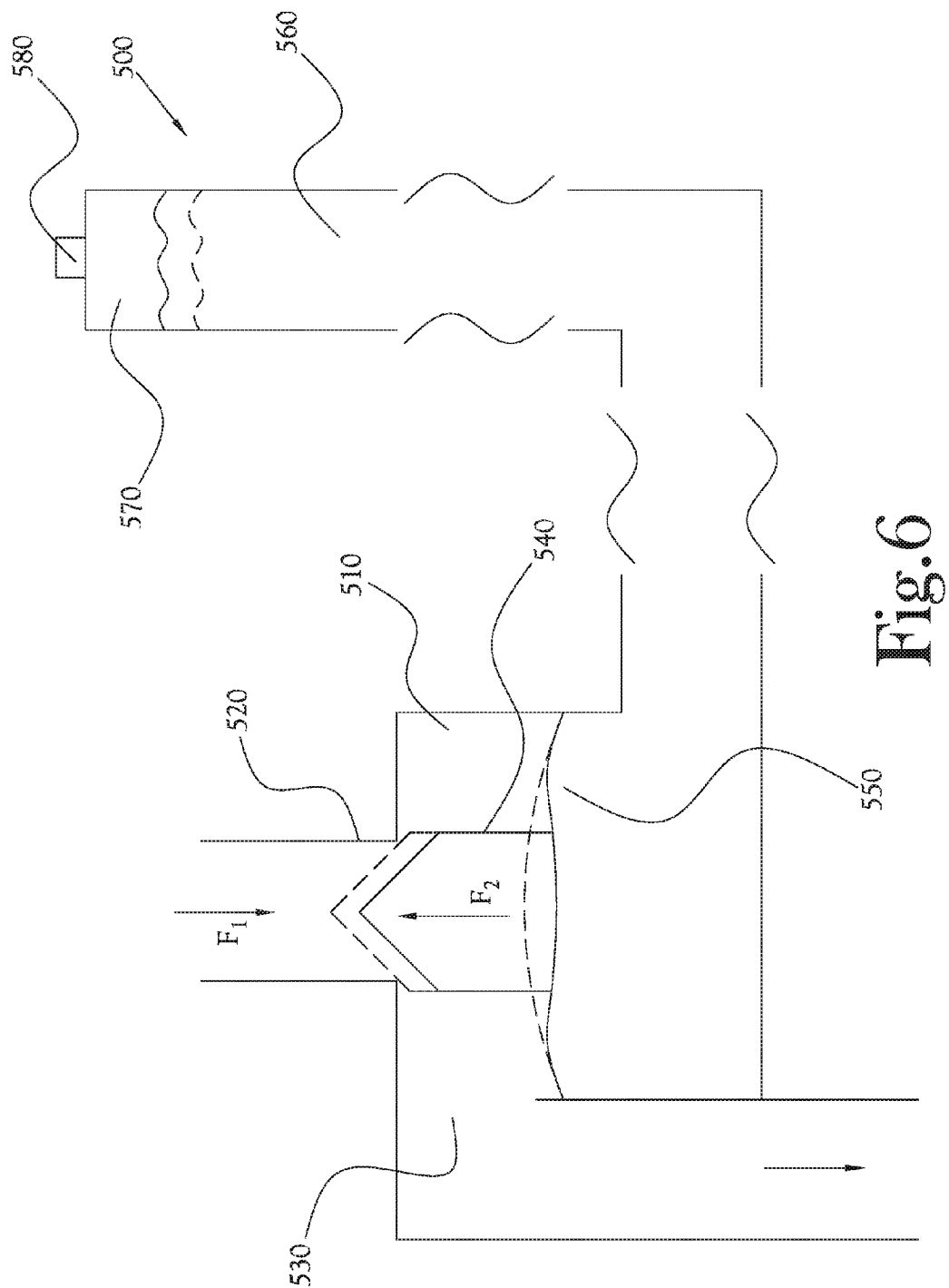

FIGS. 5-6 illustrate a gravitational pressure regulating valve according to yet another example embodiment of the present general inventive concept. The gravitational pressure regulating valve 500 in FIG. 5 includes a fluid chamber 510 with an inlet port 520 to receive a bodily fluid and an outlet port 530 to discharge the received bodily fluid, a variable resistance flow valve 540 provided in the fluid chamber to oppose a first force F1 of the fluid flow at the inlet port with a second force F2 applied to the variable resistance flow valve 540, an opposing force member 550 to apply the second force F2 to the variable resistance flow valve 540, and a reference unit 560 that is sensitive to gravitational pressure changes to cause the opposing force member 550 to vary the second force according to the gravitational pressure changes. In this example embodiment, the opposing force member is a diaphragm 550 coupled to the variable resistance flow valve 540, and the reference unit 560 is a reference fluid column 560 in direct communication with the diaphragm 550. The diaphragm 550 prevents fluid in the reference fluid column 560 from entering a portion of the fluid chamber 510 through which the bodily fluid flows. Changes in gravitational pressure applied to the reference fluid column 560 cause the diaphragm 550 to move upward or downward to increase or decrease the opposing second force F2. The device 500 may also include a predetermined amount of gas 570 forming an interface with the reference fluid column 560 to allow compression to the diaphragm resulting from the first force F1 being greater than the opposing second force F2. Various example embodiments of the present general inventive concept may also provide an air bleeder port 580 to a housing containing the reference fluid column 560 to be used to remove air from the housing when being filled with liquid.

FIG. 5 illustrates the device 500 at a vertical orientation at which the gravitational pressure is greatest on the reference fluid column 560, and therefore the opposing second force F2 is at a maximum value. As the device 500 is rotated according to the patient's position, the gravitational pressure on the reference fluid column 560 will be reduced, and the opposing second force F2 will be reduced in turn, reaching a minimum value when the device is at a horizontal position. In FIG. 5, the second force F2 is still equal to or exceeding the first force F1 of the bodily fluid at the inlet port 520. FIG. 6 illustrates the same device 500 after the first force F1 has overcome the opposing second force F2. As indicated in the drawing, the variable resistance flow valve 510 has been pushed down to open the inlet port 520, which in turn caused the diaphragm 550 to be pressed down, compressing the area of the reference fluid column 560 and decreasing the volume of the gas 570. The inlet port 520 will remain at least partially open until the opposing second force F2 again matches or exceeds the first force F1. In other words, once the excess pressure due to an excess of the bodily fluid needing to be drained is decreased, and the opposing second force F2 again counters the first force F1 caused by gravity and the weight of the draining fluid, the inlet port 520 will be closed.

It is noted that various components illustrated in FIGS. 1-7 may be omitted or substituted for, changed in shape or configuration, and so on. For example, the variable resistance flow valve 510 is illustrated as having a conical top accommodated by the inlet port 520, but any of several possible shapes and configurations may be used instead. Also, the reference unit of the device 500 is a directly connected reference fluid column that transfers gravitational pressure directly to a diaphragm. However, various other example embodiments may employ reference units that simply sense the gravitational pressure and control the opposing force member and/or variable resistance flow valve through other mechanical connections, or by electrical communication. For example, the reference unit may include a gravitational pressure sensor, and may be in electrical communication with the opposing force member to cause the opposing force member to vary the second force according to the gravitational pressure changes.

Figure 7:
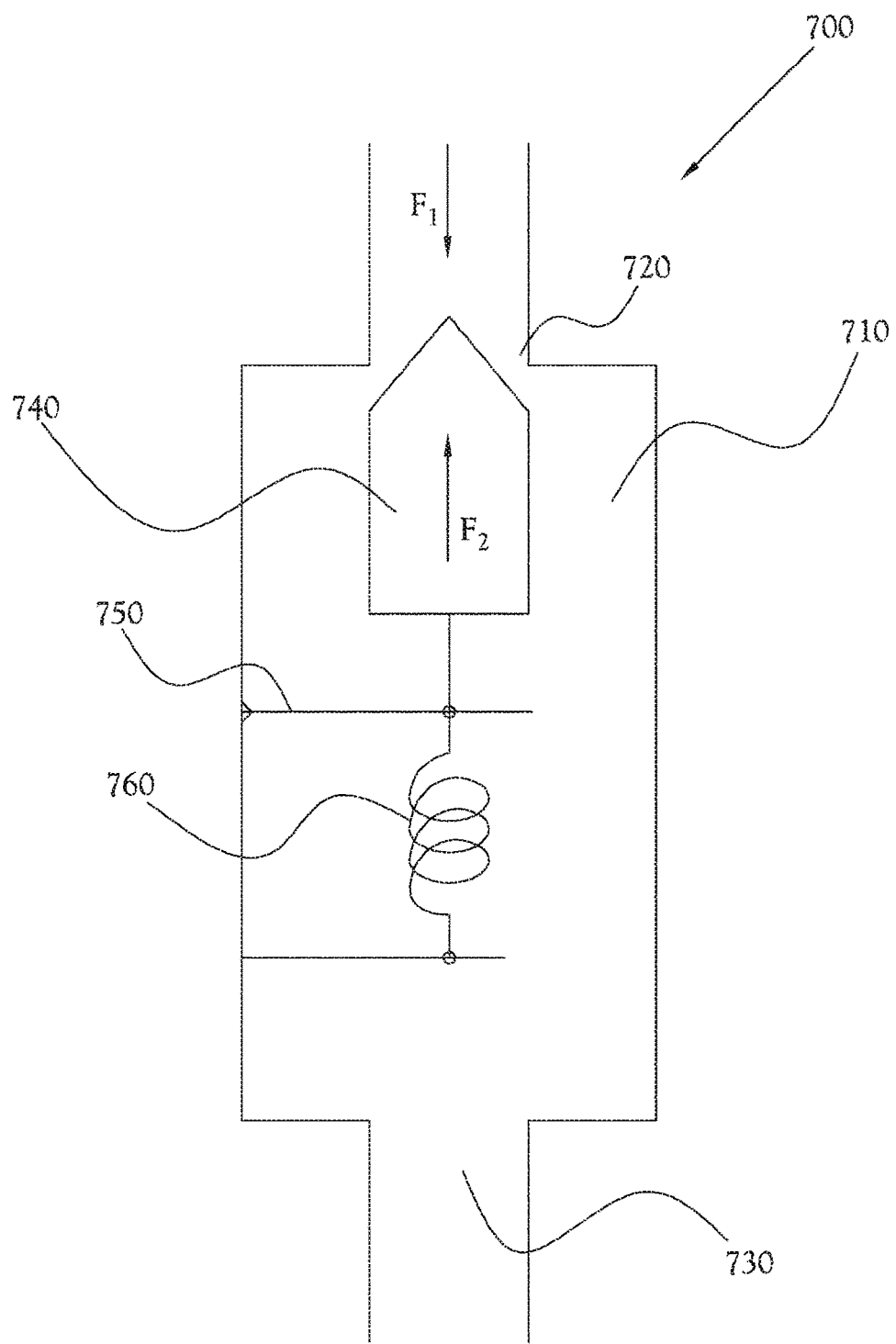
FIG. 7 is a schematic illustration of various elements of a gravitational pressure regulating valve according to still another example embodiment of the present general inventive concept.

FIG. 7 is a schematic illustration of various elements of a gravitational pressure regulating valve according to still another example embodiment of the present general inventive concept. The gravitational pressure regulating valve 700 of FIG. 7 includes a fluid chamber 710 having an inlet port 720 and an outlet port 730, and a buoyant member 740 provided in the fluid chamber 710. Fluid flows into the inlet port 720 at the first force F1, and the buoyant member 740 opposes the fluid flow with the opposing second force F2.

When the opposing second force F2 is equal to or exceeds the first force F1, the buoyant force on the buoyant member 740 causes the buoyant member 740 to move to close the inlet port 720. By contrast, when the first force F1 exceeds the opposing second force F2, the buoyant member 740 is moved to open the inlet port 720, at which point the bodily fluid will flow until the first force F1 is again matched by the second force F2. As illustrated in FIG. 7, the buoyant member 740 may have a substantially conical tip that is received by the inlet port 720. The gravitational pressure regulating valve 700 may include a guide member in the fluid chamber 710 to facilitate movement of the buoyant member 740 in a bidirectional manner. In the example illustrated in FIG. 7, the guide member is hinged member 750 that is coupled to the fluid chamber 710 and the buoyant member 740 such that the movement of the buoyant member 740 is restricted to substantially bidirectional movement toward and away from the inlet port 720. This coupling configuration may include a hinged connection at either end of the hinged member 750. Further, the gravitational pressure regulating valve 700 may include a biasing member to increase the opposing second force F2. In the example embodiment illustrated in FIG. 7, the biasing member is a spring 760 that is coupled to the fluid chamber 710 and the hinged member 750. The biasing force of the spring may be chosen to tune the opposing second force F2 to the desired strength at a horizontal orientation of the valve 700, at which point the buoyant force due to gravitational pressure is at a minimum value.

As previously described, various example embodiments of the present general inventive concept may include two or more buoyant members provided inside the fluid chamber of an example gravitational pressure regulating valve to provide additional buoyant force to the previously described opposing second force F2. Additionally, as will be described in regard to various example embodiments discussed herein, weighted or non-buoyant members may be included in conjunction with the one or more buoyant members to provide more control on the opposing forces and/or improve the sealing properties at the inlet port.

Regarding the one or more buoyant members that may be provided in various example embodiments of the present general inventive concept, and the terms "buoyant" and "non-buoyant" as used herein, the buoyant members at all times possess both a buoyant force vector, opposite that of the gravitational field, and a weight force vector that is in the same direction as the gravitational field. When the buoyant force vector exceeds the weight force vector, then the member becomes overall net buoyant and will float. In other words, the member becomes buoyant within the fluid when it possesses a net density, including its construction material, less than that of the fluid within the fluid chamber. In the various descriptions herein, the terminology of "net buoyancy" and "net non-buoyancy" may be referred to simply as buoyancy and non-buoyancy, respectively. The resulting buoyant force is generally described by Archimedes principle as the weight of the fluid that is displaced less the weight of the buoyant member itself. Therefore, the weight of the buoyant member becomes an undesirable, or parasitic, property of the buoyant member. An appropriate material density of the buoyant member for achieving an overall effective buoyancy within the fluid chamber may be implemented by utilizing a very low density object, such as plastic, foam, or a lightweight metal. However, foam and plastics present a porous structure permeable to fluids, such as those fluids intended for the fluid chamber, which would eventually succumb to excessive fluid intrusion over long durations of implantation, rendering the buoyant member effectively non-buoyant over time. Other materials, such as metals, present a challenge in that the size of the buoyant member must be sufficiently small for producing an acceptable implant, yet the material density of most metals presents a challenge for achieving net buoyancy even for hollow objects. Additionally, the thinner a buoyant member's material, the more difficult to fuse, weld, or otherwise seal the member during construction. Although metals are practically impervious to fluid intrusion, the overall density of a metal hollow sphere, or other geometric closed or sealed shapes, has limited returns for buoyancy the smaller the object becomes. While one method of achieving greater effective buoyancy would be to stack multiple buoyant members together for an overall greater collective buoyant force, the additional shape material for each buoyant element diminishes the collective buoyancy, requiring excessive buoyant members which could be unacceptable for an implant's size or shape. Therefore, an optimal buoyant member's shape may be a cylinder to minimize excessive shell material present in a series of separate spherical buoyant members, for instance. Metal buoyant objects, such as spheres or cylinders, may nevertheless be constructed from such biocompatible materials as titanium or stainless steel and be fabricated utilizing electron beam or laser welding technology. Modern sintering methodologies can further allow for ultra-thin metallic spherical shapes to be fabricated, which may provide for a configuration of buoyant members to achieve an acceptable net buoyant force, an implantable geometric size, and a practically impermeable shell to bodily fluid intrusion. Furthermore, sintering processes utilizing aluminum oxide, also known as alumina, or silicon dioxide materials may provide for biocompatible buoyant members. Such buoyant members may additionally employ surface modifying elements or treatments such as PTFE or surface roughness modifications for achieving a desirable biocompatible fluid interface optimized for hydrophilic or hydrophobic properties so as to retard or inhibit biomatter accumulation. Additionally, the buoyant members may be designed such that they can provide fluid channels for fluids to traverse over their surface by way of dimples, grooved channels, or other recessed surface portions. The overall geometric design or size of the valve's fluid chamber relative to its buoyant member(s) may be such that the geometric ratio facilitates sufficient fluid flow paths so as to retard or prevent typical biomatter accumulation and fouling.

Figure 8:
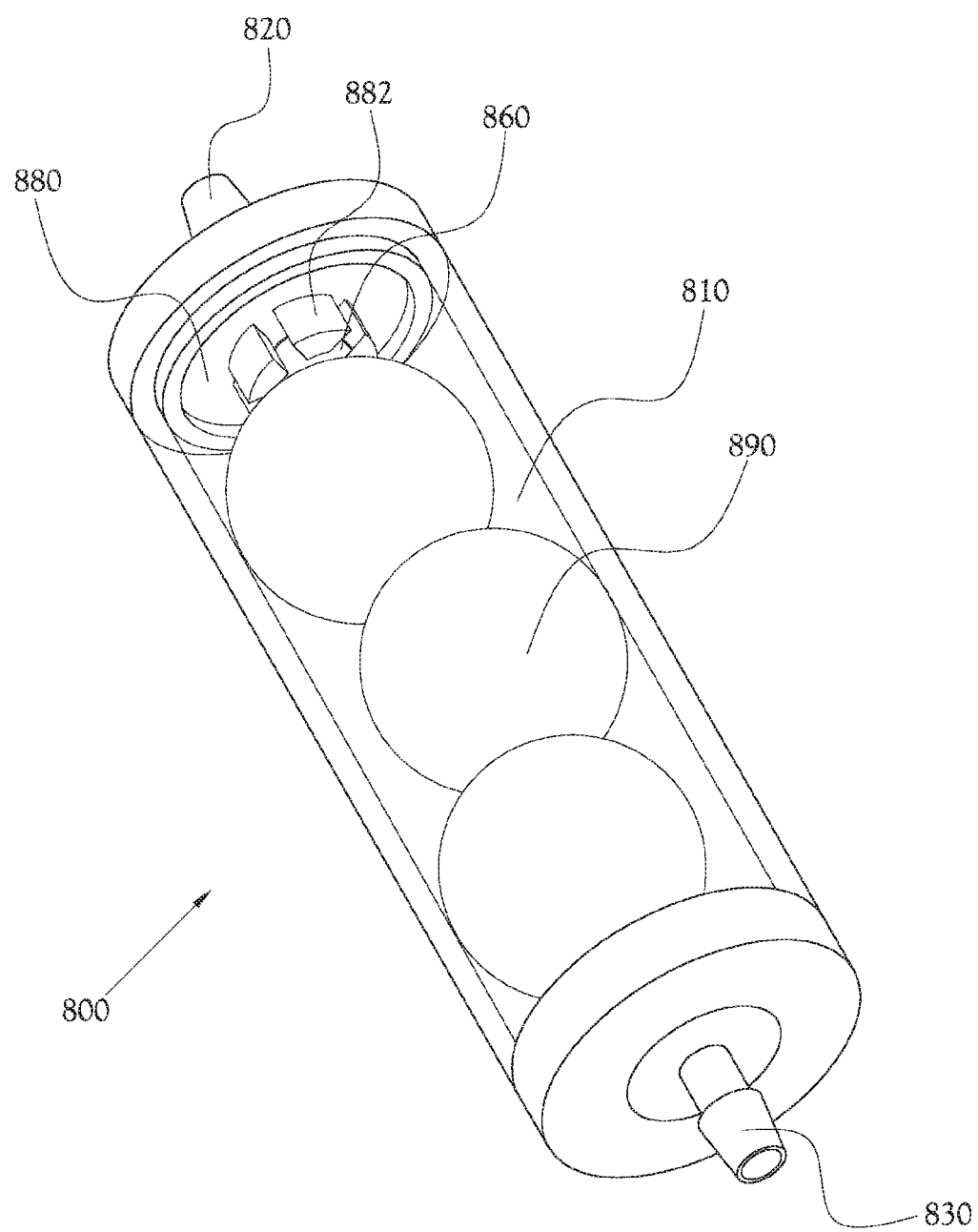
FIG. 8 is an isometric illustration of a gravitational pressure regulating valve according to still another example embodiment of the present general inventive concept.

FIG. 8 is an isometric illustration of a gravitational pressure regulating valve according to still another example embodiment of the present general inventive concept. The example gravitational pressure regulating valve of FIG. 8 includes three buoyant members provided in a fluid chamber such that the combined buoyancy of the buoyant members provides the force F2 to counter the force F1 at the inlet port. The various components of the gravitational pressure regulating valve 800 are identified and discussed further in FIGS. 9-12.

FIGS. 9-10 illustrate a cross section of the gravitational pressure regulating valve 800 of FIG. 8 in closed and open states, respectively, at the inlet port. The fully closed state illustrated in FIG. 9 may occur, for example, when the patient is standing straight up and the force F2 exceeds the force F1 at the inlet port. Conversely, the fully open state illustrated in FIG. 10 may occur, for example, when the patient is in the supine position and little, if any, force F2 is present to oppose the force F1 at the inlet port. As another example, such an open state may furthermore occur when the patient is in an incline or standing position and when the inlet port force F1 exceeds the force F2. As illustrated in FIGS. 8-10, the example regulating valve 800 includes a fluid chamber 810 having an inlet port 820 formed generally in an inlet cap, gated by a precision net non-buoyant ball 860 captured by a retaining chamber provided in or to the inlet cap and generally indicated by 880, whereby the precision net non-buoyant ball 860 mates with an inlet orifice member, also referred to herein as a mating cone seat 870, which is in communication with the net buoyant members 890 provided within the fluid chamber 810. The inlet cap described herein may be interchangeably referred to as an end cap, as in various example embodiments of the present general inventive concept, the same end cap may be used for both the inlet port and the outlet port, the inlet port in some such example embodiments being provided with the discussed net non-buoyant ball 860 and mating cone seat discussed herein. As illustrated in FIGS. 9-10, fluid flows into the inlet port 820 at a first force F1, and the precision net non-buoyant ball 860, compatible with its mating cone seat 870, opposes the fluid flow as a result of a second force F2 produced by the net buoyant members 890 buoyancy. The precision net non-buoyant member 860 and mating cone seat 870 may be selected to provide mating surfaces that are more precise than the example embodiment illustrated in FIG. 1, in which the buoyant member 140 mates directly with inlet port 120. In various example embodiments, the precision net non-buoyant ball 860 may be constructed from a hard material, such as ruby or sapphire, for example, while the precision mating cone seat 870 may be constructed from the same or different material. The precision net non-buoyant ball 860 and mating cone seat 870 may be constructed from a substantially hard material so as to facilitate precision polishing of the respective surfaces for a precise fit and fluid seal between the two components. Ruby and/or sapphire materials may be utilized and polished, for example, to achieve a minimal mating friction to facilitate a low resistance opening and closing, minimizing offset or hysteresis in valve opening and closing operations. The overall density desired for such a precision ball, whether hollow or solid, for precisely mating with its conical orifice may present challenges, however, with regard to designing a buoyant gravitational valve with a sufficient buoyant vector F2 while achieving a minimal size implant, given the precision ball's weight acts as a parasitic to the desired buoyant vector F2 for all angles not perpendicular to the gravitational field. Furthermore, the use of a high density precision ball, such as a ruby with a net negative buoyancy for example, could be problematic in any conventional fluid chamber attempting to utilize a communicating buoyant element(s) since opening of the valve, by means of translating a precision net non-buoyant ball such as 860, could result in its irrevocable removal, or retraction, from the mating cone seat, 870, and its retaining chamber, 880, rendering the valve permanently open. These challenges are unique for a buoyant gravitational valve unlike that of a weighted gravitational valve, such as that described by U.S. Pat. No. 3,889,687, since the weight of a precision, high density, net non-buoyant mating ball would only assist in closing the valve, typically falling into its mating conical seat under normal operating conditions, in a weighted gravitational valve implementation. The present general inventive concept as illustrated in FIGS. 8-10, however, includes the retaining chamber 880 configured to capture or retain the precision net non-buoyant ball 860, which substantially restricts lateral, or transaxial, movement of the precision ball 860 yet significantly facilitates bidirectional, or reciprocating, movement only along the valve's axial path, or the axis extending from the valve's inlet port 820 to an outlet port 830, also referred to as its longitudinal axis, for example. As previously described, such an arrangement may be referred to as a slip fit. This slip fit arrangement configured for the precision net non-buoyant ball 860 inside the retaining chamber 880 is different than the arrangement configured for the net buoyant members 890 illustrated in FIGS. 8-10. As illustrated in FIGS. 8-10, the diameter of the fluid chamber 810 is sufficiently larger than the diameter of the net buoyant members 890 to allow lateral movement of the net buoyant members 890 from side to side in the fluid chamber 810 such that fluid is able to pass around the net buoyant members 810, but the sequential order of the net buoyant members 810 is maintained. Thus, this relatively loose fit of the net buoyant members 810 in the fluid chamber 810 is in contrast with the slip fit of the retaining chamber 880 around the precision net non-buoyant ball 860.

FIGS. 11-12 respectively illustrate an exploded view and an assembled view of the retaining chamber 880, mating cone seat 870, and precision net non-buoyant ball 860 illustrated in FIGS. 9-10 according to an example embodiment of the present general inventive concept. As illustrated in FIGS. 11-12, the retaining chamber 880 is configured with a plurality of radially spaced guide members 882 for use by, or in the formation of, the retaining chamber 880 in capturing and guiding the precision net non-buoyant ball 860. According to various example embodiments, the guide members 882 may be radially spaced, for example, to retain the precision net non-buoyant ball 860 and to substantially limit its translation to only axial or longitudinal movement while yet allowing fluid to flow in the open spaces between adjacent guide members 882 when the net non-buoyant ball 860 is unseated from the mating cone seat 870. In various example embodiments, the guide members 882 may be alternatively designed so as to allow a single piece guide member, for instance, by utilizing fluid veins within its material, a permeable yet rigid mesh configuration, or other such similar configuration that maintains the slip fit of the net non-buoyant ball 860 but allows fluid flow when the net non-buoyant ball 860 is in an open state, i.e., when the net non-buoyant ball 860 is moved away from the mating cone seat 870. In various example embodiments, the guide members 882 may be formed as part of the body of the fluid chamber 810, rather than a retaining chamber that is part of the inlet port assembly. In conjunction, the regulating valve 800 of FIGS. 9-10 may be geometrically designed such that the length of the fluid chamber 810, when considered in combination with the volume or length of its buoyant members 890, will only facilitate or allow a specific maximum axial or longitudinal translation of the precision net non-buoyant ball 860 so as to always retain it within the retaining chamber 880, over all valve or patient positions. Thus, the regulating valve 800 may be configured such that the buoyant members 890 cannot move far enough away from the retaining chamber 880, regardless of the orientation of the regulating valve 800, to allow the precision net non-buoyant ball 860 to move out of the retaining chamber 880.

It is understood that various components of the example regulating valve 800 illustrated in FIGS. 8-12 could be substituted for, and/or omitted, while still maintaining the scope of the present general inventive concept. For example, the inlet orifice referred to as the conical section of the mating cone seat 870 may be chamfered, spherical, or any other configuration to provide a seat for the precision net non-buoyant ball 860. In other example embodiments, a conical accommodation may be omitted altogether, and a mating section simply having a circular opening to receive the non-buoyant ball 860 may be implemented. In still other example embodiments, the mating seat may be omitted altogether, and the non-buoyant ball 860 may simply be received by a circular opening in the retaining chamber 880. In various example embodiments, a precision net buoyant ball may be provided in the valve 800, rather than the precision net non-buoyant ball. Though the various buoyant and non-buoyant members described in FIGS. 8-12 are described and illustrated as spherical balls, it is understood that various example embodiments may provide buoyant and/or non-buoyant members of other configurations, such as cylindrical, etc. Also, while the inlet cap having the inlet port 820 is illustrated as being formed of various components including the retaining chamber 880 with a protrusion, or barb, fitted therein to mate with a fluid conduit, and also fitted in an end cap closing a first end of the valve 800, it is understood that various ones of these components may be combined into fewer than the number of components shown.

In the example embodiment illustrated in FIGS. 8-10, the inlet port 820 and retaining chamber 880 configuration is also used as an end cap, or outlet port 830, albeit without the precision non-buoyant ball 860 and mating cone seat 870. Such use at both ends of the valve 800 provides convenience in manufacturing the device, since the same parts can be used to form both the inlet and outlet ports. An additional feature provided by such an arrangement is that the guide members 882 at the outlet port 830 provide a stop member to prevent the bottom most buoyant member 890 from moving too close to the outlet port 830. In other words, even in an orientation that results in the buoyant members 890 moving toward the outlet port 830, the buoyant members 890 are prevented by the guide members 882 from moving far enough to allow the precision ball 860 out of the retaining chamber 880, and the spaced apart guide members 882 also allow fluid flow to be maintained through the outlet port 830.

Figure 13:
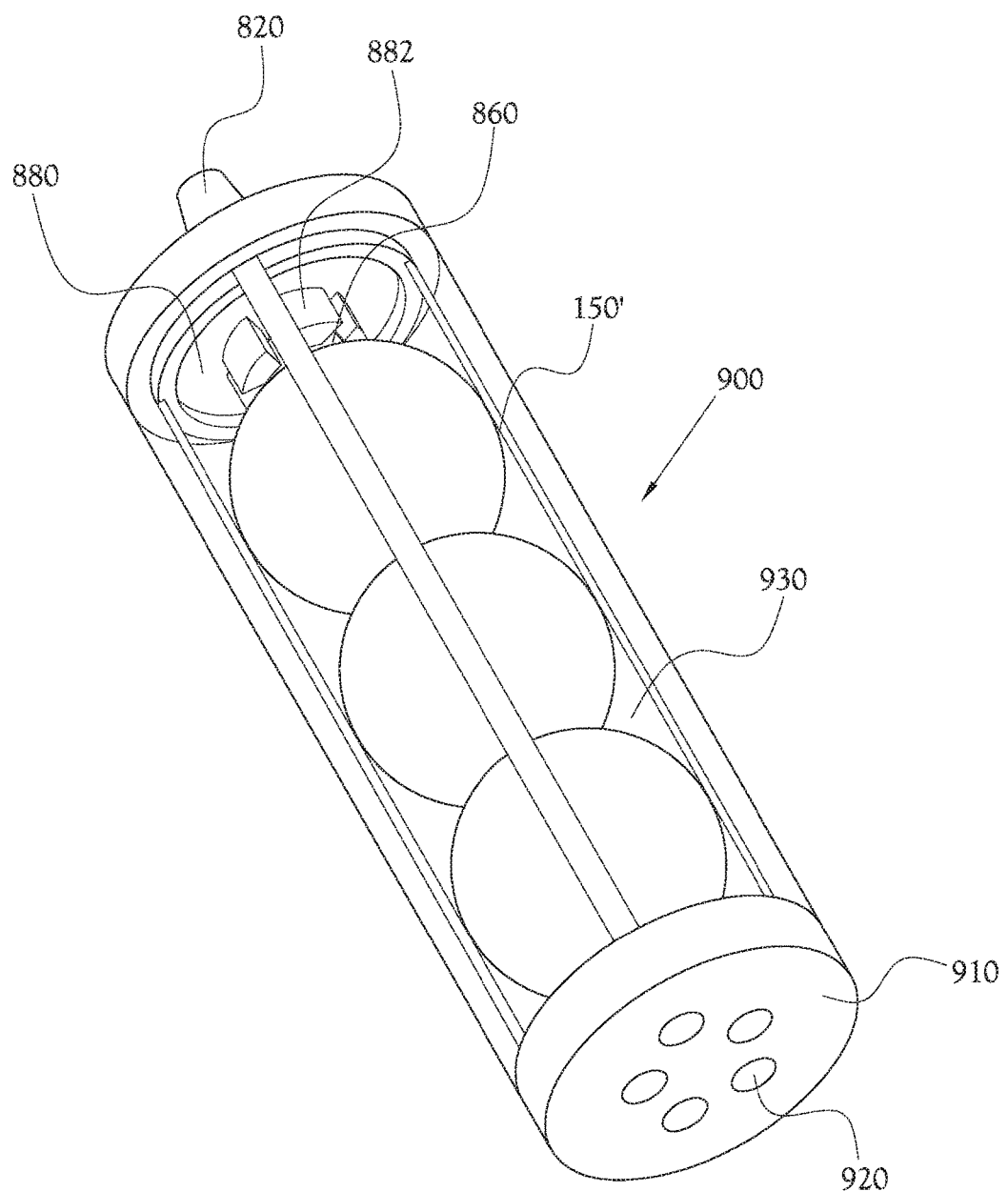
FIG. 13 is an isometric illustration of a gravitational pressure regulating valve according to still another example embodiment of the present general inventive concept.

FIG. 13 is an isometric illustration of a gravitational pressure regulating valve according to still another example embodiment of the present general inventive concept. Similar to the example embodiment illustrated in FIG. 8, the example gravitational pressure regulating valve 900 of FIG. 13 includes three buoyant members provided in a fluid chamber such that the combined buoyancy of the buoyant members provides the force F2 to counter the force F1 at the inlet port. However, the example embodiment illustrated in FIG. 13 is provided with one or more fluid chamber guide members 150' to guide the net buoyant members 890 in a direction to and away from the inlet port 820, similar to the guiding action provided by the guide member 150 illustrated in FIG. 1. According to various example embodiments, the one or more fluid chamber guide members may be separate members, integrated into a single member inserted in the valve, integrated into the valve body, and so on. In various example embodiments, the fluid chamber guide members 150' in the fluid chamber 930 are configured to provide a slip fit for the buoyant members 890 located therein. In various example embodiments, the one or more fluid chamber guide members 150' may be alternatively designed as separate or integrated members constructed of a material utilizing fluid veins, a permeable yet rigid mesh configuration, or other such similar configuration that maintains the slip fit of the buoyant members 890 but allows fluid flow around the buoyant members 890 when the net non-buoyant ball 860 is moved away from the mating cone seat 870. Also, the example valve 900 has an outlet port 910 that is different than the outlet port 830 illustrated in FIG. 8. The various components of the gravitational pressure regulating valve 900 are identified and discussed further in FIGS. 14-17.

FIGS. 14-15 illustrate a cross section of the gravitational pressure regulating valve 900 of FIG. 13 in closed and open states, respectively, at the inlet port. The fully closed state illustrated in FIG. 14 may occur, for example, when the patient is standing straight up and the force F2 exceeds the force F1 at the inlet port 820. Conversely, the fully open state illustrated in FIG. 15 may occur, for example, when the patient is in the supine position and little, if any, force F2 is present to oppose the force F1 at the inlet port 820. The operation of the valve 900 and the various components thereof are similar to the example valve 800 illustrated in FIGS. 8-12. However, rather than allowing lateral movement of the buoyant members 890 to facilitate fluid flow through the fluid chamber 930, the fluid chamber 930 is instead provided with the fluid chamber guide members 150' to guide the buoyant members 890 to move substantially only along a longitudinal axis of the valve 900. In other words, the buoyant members 890 of the example embodiment illustrated in FIGS. 13-15 are provided with a slip fit similar to that provided to the precision net non-buoyant ball 860, so that lateral movement of the buoyant members 890 relative to the longitudinal axis of the valve 900 is largely prevented. The spacing between the fluid chamber guide members 150' allows fluid flow around the buoyant members 890. FIG. 16 illustrates a cross section of the fluid chamber 930, fluid chamber guide members 150', and buoyant members 890 of FIGS. 13-15 according to an example embodiment of the present general inventive concept.

The outlet port 910 of the valve 900 is formed with a plurality of apertures 920 to allow fluid flow out of the valve 900. FIG. 17 illustrates a bottom view of the outlet port 910 of FIGS. 13-15 according to an example embodiment of the present general inventive concept. As indicated by the example embodiment illustrated in FIG. 17, the apertures 920 are regularly offset from the center of the outlet port 910, and thus cannot be blocked by the adjacent buoyant member 890 in a situation in which the orientation of the valve 900 results in the buoyant member 890 contacting the outlet port 910. Such a perforated outlet port configuration may better prevent occlusion from cystic formations within the peritoneum and furthermore better facilitate a more acceptable implant geometry for the peritoneum than an outlet barb fitting, for example. Additionally the valve geometry may be designed to facilitate a desirable implant orientation by providing fasteners, slots, or other securement means compatible with abdominal meshes or other tissue attachment means.

The present general inventive concept facilitates distinct advantages over, and overcomes challenges of, weighted gravitational valve designs, in that the buoyant gravitational valve facilitates straight through fluid flow from inlet to outlet when implanted, unlike weighted gravitational valves, while the valve's retaining chamber 880 and, in some example embodiments, fluid chamber guide members 150', provide for a substantially more predictable and smoother fluid flow-to-pressure transfer function, substantially resembling a sinusoid, than that of the conventional devices cited. The conventional devices, utilizing weighted gravitational valve designs, such as that described by U.S. Pat. No. 3,889,687, are required to employ a serpentine fluid route whereby the valve's inlet must enter from the inferior orientation of the patient when properly implanted, despite the fluid source being from a patient's ventricles above the valve, while the outlet must be at a superior orientation. This is required for the weighted valve to properly operate while implanted, because the weighted gravitational valve's fluid opposition must be in the same direction as that of the gravitational field (i.e., inferior direction of the patient), necessitating pressurized fluid from a patient's ventricles to enter the weighted members opposition from the bottom, or patient's inferior, side of the valve, either by way of the valve's internal fluid routing or by external lumen, or tubing, routing configuration. Such serpentine, or 'S' curve, routing often permits fluid zones with little flow, resulting in non-laminar flow and biomatter collection, leading to obstructions. The present general inventive concept of a buoyant gravitational valve overcomes this challenge by facilitating fluid flow uni-directionally along a plane formed along the valve's axial or longitudinal axis as extended from approximately its inlet to outlet.

The gravitational pressure regulating valve according to various example embodiments of the present general inventive concept may include biocompatible materials such as polysulfone, for example, for fabrication of the valve's components, such as the fluid chamber, for example, or for the inlet and/or outlet ports. Such components may be distinctively separate and assembled together after installing interior valve components, whereas the valve's body or fluid chamber may be enclosed by end caps which also receive inlet or outlet ports as well as orifice components. Furthermore, the valve's components may additionally utilize x-ray opaque materials or markers such as barium sulfate or tantalum, for example, to allow verification of the valve's orientation or operation. Alternatively, or in combination with the aforedescribed materials or markers, the valve may utilize clear components or materials for the visual verification of operation or the bleeding of air or fluid priming, for example. The valve's components may also utilize surface modifying coatings or additives, such as fluorine based molecules, or self-locating fluoro-oligomeric polymer surface modifying molecules, for the prevention of biomatter accumulation, such as protein adsorption, or antibiotics or antimicrobials such as silver for the inhibition of infectious bacteria, for instance.

Various example embodiments of the present general inventive concept provide an antisiphon device that prevents siphoning in a hydrocephalus shunt system. The antisiphon device may have an inlet, an outlet, a fluid chamber, a variable resistance flow valve responsive to CSF force or pressure, an opposing force or pressure generation element for variable adjustment, responsive to a gravitational field, of the flow valve, and an optional pressure element with further optional discrete or continuous pressure adjustment of the variable resistance flow valve.

The antisiphon device may be connected between a differential pressure relief valve normally used to control the intracranial pressure by removal of excess CSF fluid, and a distal exit catheter used in a hydrocephalus shunt treatment. There is generally no restriction on the general placement of the components used in a hydrocephalus system such as a flow transfer path between the cranium and peritoneal cavity or generally placed for a lumboperitoneal shunt. Optionally, the valve functionality contained in a shunt system could be incorporated into the functionality of the variable resistance flow valve and optional pressure element. The antisiphon device may be optionally positioned with manual placement, or automatic adjustment, or remote adjustment, to vertically align the inlet and outlet to align the device to be in the vertical direction when the patient is in the standing position.

The antisiphon device may prevent siphoning by balancing the force due to the weight of the CSF fluid contained within the shunt system with an opposing force element. The opposing force is substantially equal to the force generated by the weight of the CSF fluid, regardless of patient angle and activity without substantially restricting CSF fluid flow with regard to frictional or other losses. The opposing pressure element may be realized with a fixed or adjustable buoyancy device, relative to the CSF fluid, contained within the CSF fluid such that the buoyant opposing force is substantially equal to the gravitational force or weight generated by the CSF fluid contained within the shunt system. Furthermore, the difference between the forces or pressure of the CSF fluid in the shunt system compared to the opposing buoyancy force may be used to reduce or increase the resistance of the variable resistance flow valve and either restrict or enable CSF fluid flow between the antisiphon device's inlet and outlet. Furthermore, the antisiphon device's opposing force pressure generation element does not substantially restrict CSF fluid flow by substantially occupying the same volume contained within the substantial CSF fluid flow, and wherein the buoyancy device could be located in an adjacent or externally connected chamber and transmit valve control signals remotely. The antisiphoning device's opposing force or pressure element can substantially compensate for the effects of patient growth and maintain the ability to approximately oppose the additional force generated by the weight of the CSF fluid in the shunt system. The opposing pressure generation element can be adjustable and realized by adding or subtracting buoyancy elements to adjust the total opposing buoyancy force either during installation, later procedures, or through an internal mechanism which may be externally adjustable.

The opposing force or pressure generation element can also be a reference column of fluid aligned with the flow path with substantially equal length, or weight, containing an ideal gas forming an interface between the reference column of fluid and the column containment. The reference column could be attached to a fixed or adjustable fluid reservoir and/or a gas reservoir that is substantially large to allow free movement of the reference column. The interface between the reference fluid and ideal gas interface could be maintained by effects of surface tension or other forces which act to keep the liquid gas interface intact and prevents sloshing within the reference column. A flexible low resistance physical interface could be used to separate the liquid and gas as well. The movement of this interface is relative to the gravitational forces applied to the CSF fluid in the shunt system, including patient alignment, and the pressure differences between the reference column, and actual CSF fluid column with the shunt system. This movement can be used to adjust the resistance of the variable resistance pressure element by direct connection, mechanical or electrical control, or remote connection. The substantial effect is to compensate for the weight of the CSF fluid in the shunt system by negatively referencing it in the antisiphon device to the reference column of fluid. Thus, the flow of CSF in the shunt system substantially only depends on the CSF shunt system pressure differential across the pressure element. Additionally, the pressure element can further be configured to compensate for the additional flow generation or pressure generation due to the fluid velocity of the CSF fluid flowing in the shunt system. The pressure generated by the CSF flow velocity depends on column height and tubing size and can substantially contribute to parasitic drainage. Furthermore, the pressure element can be configured to compensate for other pressure error generators such as, but not limited to, tubing flow resistance differences, tubing size differences, tubing length differences, column height differences, etc. The operation of the variable resistance member and pressure element additionally can be combined into a single element to simultaneously compensate for CSF siphoning and set the CSF pressure drainage pressure threshold. The length of the tubes, in both the reference column and actual shunt CSF column, can automatically increase in length as the patient grows by implantation of extra tube length or other tube length increasing device. The relative relationship between the reference tube and actual CSF shunt tubing can be further scaled for more optimum control of the variable resistance pressure element. Furthermore, the reference column can be a complete column of fluid without an ideal gas interface with a fluid filled connection to a bladder or reservoir capable of transmitting surrounding environmental pressure into the reference fluid column. For example a completely fluid filled reference column connection to a bladder that is placed in the atmosphere or peritoneal cavity will transfer the surrounding environmental pressure into the reference column of fluid.

Diagnostic tools can be optionally incorporated into the antisiphoning structure to aid the care giver in determining shunt system functionality. Such as operation verification through a needle access port with an operationally responsive device integrated into the antisiphon structure. Active or passive diagnostic structures could be used to manually or automatically determine operation by measuring events triggered by CSF flow. For example determining positional movement of the variable resistance member and pressure element is an indication of CSF flow and further the movement rate is an indication of CSF flow rate. Additionally, the antisiphon device can be incorporated in an External Drainage System (EDS) or other monitoring systems to aid in the treatment of elevated intracranial CSF pressure.

According to various embodiments of the present general inventive concept, a gravitational pressure regulating valve is provided to regulate fluid flow in a patient, including a fluid chamber having an inlet port to receive a bodily fluid and an outlet port to discharge the received bodily fluid, and an opposing force member in the fluid chamber to oppose a first force of the fluid flow at the inlet port with a second force that varies according to changes in gravitational alignment, is provided. Various example embodiments of the present general inventive concept may use buoyant or weighted members as the opposing force members. Other various example embodiments my use gravitational pressure sensors in mechanical or electrical communication with opposing force members to control the amount of opposing force applied to the fluid flow. Also, various example embodiments described herein as employing buoyant members may be used with weighted members by simply reversing the orientation of the fluid chambers and inlet/outlet ports, just as various example embodiments described as employing weighted members may be used with buoyant members by reversing the orientation of the fluid chambers and inlet/outlet ports.

Various example embodiments of the present general inventive concept provide a gravitational pressure regulating valve to regulate fluid flow of a patient, including a fluid chamber having an inlet port to receive a bodily fluid and an outlet port to discharge received bodily fluid, the fluid chamber including a first chamber configured to capture a non-buoyant member therein and to guide the non-buoyant member along a longitudinal axis of the first chamber to facilitate bi-directional reciprocating movement of the non-buoyant member to and from the inlet port, and a second chamber configured to capture one or more buoyant members therein such that when the second chamber is filled with bodily fluid, at least one of the buoyant members applies a resolved buoyant pressure from a buoyant force of the one or more buoyant members in opposition to an inlet pressure of fluid at the inlet port. One of the one or more buoyant members may be configured to apply the buoyant force of the one or more buoyant members via tangential contact with the non-buoyant member. The buoyant force applied to the non-buoyant member may vary according to changes in gravitational field alignment in the fluid chamber due to the orientation of the valve. The first and second chambers may be configured such that the one or more buoyant members prevent the non-buoyant member from becoming separated from the first chamber at any orientation of the valve. The non-buoyant member and/or the one or more buoyant members may be spherical. An inner width dimension of the first chamber may be configured to form a slip fit with an outer diameter of the non-buoyant member. The first chamber may be formed by one or more guide members extending from an inner surface of the fluid chamber. A plurality of open spaces may be formed between adjacent ones of the guide members to allow flow of bodily fluid past the non-buoyant member. The valve may further include an inlet cap forming a first end of the fluid chamber, and in which the inlet port is formed, wherein one or more guide members extend from the inlet cap to form the first chamber. An inlet orifice member may be provided in the inlet cap to mate with, or otherwise be fitted into or onto, the inlet port, the inlet orifice member being configured to receive the non-buoyant member to close the inlet port. The one or more buoyant members may be configured to cause the non-buoyant member to close the inlet port in response to the resolved buoyant pressure exceeding the inlet pressure. The outlet port may include an outlet cap having a plurality of apertures through which bodily fluid flows out of the fluid chamber. The second chamber may include one or more fluid chamber guide members extending from an inner surface of the fluid chamber. A plurality of open spaces may be formed between adjacent ones of the fluid chamber guide members to allow flow of bodily fluid past the one or more buoyant members. The one or more fluid chamber guide members may be formed separately or integrated into a single body inserted into the valve. An inner width dimension of the second chamber formed by the one or more fluid chamber guide members may be configured to form a slip fit with an outer diameter of the one or more buoyant members.

Various example embodiments of the present general inventive concept may be used according to various attributes of the patient to be treated. For example, it may be more desirable to use a weighted member configuration for short tubing compensation in a shorter patient, and a buoyancy device for long tube compensation in a taller patient. Also, interchangeability of different embodiments allows for combining embodiments to more efficiently offer a more customizable patient-centered anti-siphoning solution so that a customizable multi-embodiment solution is used on a patient. Different configurations may be made available in assembly kits such that different embodiments of the present general inventive concept may be combined according to the unique needs of each patient. For example, various assembly kits may include modular components such that more than one buoyant member and/or weighted member configuration can be combined, a buoyant member configuration may be combined with a weighted member configuration, and so on. As another example, various assembly kits may provide additional buoyant and/or weighted members for customizing the counter force F2 according to the unique needs of the patient.

It is noted that the simplified diagrams and drawings do not illustrate all the various connections and assemblies of the various components, however, those skilled in the art will understand how to implement such connections and assemblies, based on the illustrated components, figures, and descriptions provided herein, using sound engineering judgment.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

While the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

The invention claimed is:

1. A gravitational pressure regulating valve to regulate fluid flow of a patient, comprising:
    a fluid chamber defining an inlet port for receiving a bodily fluid and an outlet port for discharging received bodily fluid, the fluid chamber comprising:
        a first chamber in fluid communication with the inlet port, and a non-buoyant member disposed in a slip fit arrangement with inner walls of the first chamber, wherein an inner dimension of first chamber is slightly larger than an outer dimension of the non-buoyant member to enable bi-directional reciprocating movement of the non-buoyant member along a longitudinal axis of the first chamber while restricting transaxial movement of the non-buoyant member; and
        a second chamber in fluid communication with the first chamber, wherein one or more buoyant members are disposed within the second chamber, and wherein when the second chamber is at least partially filled with bodily fluid, the one or more buoyant members exert a resolved buoyant pressure from a buoyant force of the one or more buoyant members on the non-buoyant member to push the non-buoyant member toward the inlet port, thereby opposing an inlet pressure of fluid at the inlet port.

2. The valve of claim 1, wherein wherein the non-buoyant member comprises a longitudinal axis extending coaxially with the longitudinal axis of the first chamber, and wherein the non-buoyant member contacts at least one of the one or more buoyant members at a point spaced apart from the longitudinal axis.

3. The valve of claim 1, wherein the buoyant force applied to the non-buoyant member varies according to changes in gravitational field alignment with the longitudinal axis of the first chamber.

4. The valve of claim 1, wherein at least one of the one or more buoyant members contacts the non-buoyant member to keep the non-buoyant member at least partially within the first chamber.

5. The valve of claim 1, wherein the non-buoyant member and/or the one or more buoyant members are spherical.

6. The valve of claim 1, wherein the first chamber and the second chamber are axially aligned.

7. The valve of claim 1, wherein the first chamber is defined by one or more guide members extending from an inner surface of the fluid chamber.

8. The valve of claim 7, wherein a plurality of open spaces are defined between adjacent ones of the guide members to allow flow of bodily fluid past the non-buoyant member.

9. The valve of claim 1, wherein a first end of the fluid chamber comprises an inlet cap that defines the inlet port, and wherein one or more guide members extend from the inlet cap to define the first chamber.

10. The valve of claim 9, wherein the inlet cap comprises an inlet orifice member that mates with the inlet port and receives the non-buoyant member to close the inlet port.

11. The valve of claim 1, wherein the one or more buoyant members cause the non-buoyant member to close the inlet port in response to the resolved buoyant pressure exceeding the inlet pressure.

12. The valve of claim 1, wherein the outlet port comprises an outlet cap having a plurality of apertures through which bodily fluid flows out of the fluid chamber.

13. The valve of claim 1, wherein the second chamber includes one or more fluid chamber guide members extending from an inner surface of the fluid chamber.

14. The valve of claim 13, wherein a plurality of open spaces are defined between adjacent ones of the fluid chamber guide members to allow flow of bodily fluid past the one or more buoyant members.

15. The valve of claim 13, wherein the one or more fluid chamber guide members are integrated into a single body disposed within the valve.

16. The valve of claim 13, wherein the one or more buoyant members are disposed in a slip fit arrangement with the one or more fluid chamber guide members.

* * * * *

UNITED STATES PATENT AND TRADEMARK OFFICE
CERTIFICATE OF CORRECTION

PATENT NO. : 10,076,643 B2
APPLICATION NO. : 14/964141
DATED : September 18, 2018
INVENTOR(S) : Chad Seaver et al.

It is certified that error appears in the above-identified patent and that said Letters Patent is hereby corrected as shown below:

In the Claims

Issued Claim 2 should read:
"The valve of claim 1, wherein the non-buoyant member comprises a longitudinal axis extending coaxially with the longitudinal axis of the first chamber, and wherein the non-buoyant member contacts at least one of the one or more buoyant members at a point spaced apart from the longitudinal axis."

Signed and Sealed this
Twentieth Day of November, 2018

Andrei Iancu
*Director of the United States Patent and Trademark Office*